United States Patent [19]

Trestianu et al.

[11] Patent Number: 4,757,023

[45] Date of Patent: Jul. 12, 1988

[54] METHOD AND EQUIPMENT FOR THE SIMULATED DISTILLATION BY MEANS OF GAS CHROMATOGRAPHY WITH NON VAPORIZING DIRECT INJECTION

[75] Inventors: Sorin Trestianu, Brussels, Belgium; Fausto Munari; Carlo Saravalle, both of Milan, Italy

[73] Assignee: Carlo Erba Strumentazione S.p.A., Italy

[21] Appl. No.: 810,927

[22] Filed: Dec. 19, 1985

[30] Foreign Application Priority Data

Dec. 28, 1984 [IT] Italy ............... 24278 A/84

[51] Int. Cl.[4] .............. G01N 30/02; G01N 21/00
[52] U.S. Cl. ................... 436/154; 436/161; 422/54; 422/89; 422/67; 55/386; 585/825
[58] Field of Search ........... 436/154, 161; 422/89, 422/54, 67; 55/386; 585/825

[56] References Cited

U.S. PATENT DOCUMENTS 3,661,527  5/1972  Eggersten et al. .............. 422/54
4,135,881  1/1979  Bakx et al. ...................... 422/89
4,376,641  3/1983  Nestrick et al. ................ 55/386

FOREIGN PATENT DOCUMENTS 0142558  3/1982  Japan .............................. 436/161
0210211  6/1984  Netherlands ................... 436/161

OTHER PUBLICATIONS

Quantitative Gas Chrom Analysis of Hydros w/Capillary Columns and Flame Ioniz. Detector, *Anal. Chem.*, 36, 3 p. 461, 1964.

*Primary Examiner*—Kenneth M. Schor
*Assistant Examiner*—Lori-Ann Cody
*Attorney, Agent, or Firm*—Lerner, David, Littenberg, Krumholz & Mentlik

[57] ABSTRACT

The invention concerns a method and an equipment for the simulated distillation, by means of gas chromatography, of petroleum products, capable of characterizing also high boiling products, exceeding C55, over 600 C TBP. A chromatograph is used with a capillary column having a length less than or equal to 10 m, containing an immobilized non polar polydimethylsilicon gum stationary phase with a film thickness less than or equal to 0.2 μm. The sample is introduced through a non vaporizing direct cold on-column injection and the eluted sample is detected by means of a FID detector. The column oven is operated in temperature programming conditions up to temperatures exceeding 400 (up to 430–450 C.).

9 Claims, 1 Drawing Sheet

METHOD AND EQUIPMENT FOR THE SIMULATED DISTILLATION BY MEANS OF GAS CHROMATOGRAPHY WITH NON VAPORIZING DIRECT INJECTION

FIELD OF THE INVENTION

The present invention relates to a method and an apparatus for a simulated distillation by means of gas chromatography of petroleum fractions and, in particular, of heavy residue petroleum fractions derived from atmospheric and vacuum distillation. These residues are assigned to undergo further treatment, such as cracking, for conversion into white products.

DISCUSSION OF THE PRIOR ART

In order to characterize components, derivatives, and residues of petroleum products for the purpose of, for example, choosing the type of industrial treatment that such petroleum products should undertake or the type of control of relevant processes in plant, a widely used method for this purpose is analysis by distillation.

Laboratory distillation tests are used, for example, to determine the boiling temperature range of petroleum products by a distillation curve—for instance, a so-called Engler distillation curve—which reports the total percentage of distillate for each temperature value. However, plotting of these curves requires a distillation operation that is extremely long and burdensome and that does not allow a characterization of heavy fractions which require very high temperatures for obtaining product decomposition. In fact, even if conventional distillation is carried out under conditions of reduced pressure (ASTM D1160), it is generally not suitable for samples with boiling points exceeding 450°–500° C. (see Paragraph 10.13 ASTM D2892).

A better characterization of heavy petroleum products can be obtained using an instrumentation for short path vacuum distillation. For example, the DISTACT System (TOTAL CFR/LEYBOLD HERAEUS) (P. Vercier and Moueton, ANALUSIS 10, 1982-57). This instrumentation allows the obtaining of petroleum fractions with boiling points exceeding 600° C. without significant thermal degradation. However, this type of instrumentation, even if it does not produce significant thermal degradation of the components, is difficult to operate for the characterization of products by their boiling point distribution curve. Moreover, it does not permit one to correlate the boiling points under vacuum with those at atmospheric pressure.

In order to avoid the drawbacks of distillation procedures, it has been proposed that one can simulate the distillation up to the actual boiling point by means of a temperature programmed low resolution gas chromatographic analysis (F. T. Eggerston, S. Groennings, and J. J. Holst, Anal. Chem. 32:904–909 (1960)) (See also R. Butter in: "Chromatography in Petroleum Analysis," K. Altgelt and T. Gouw editors, M. Dekker, New York, 1979, p. 75).

This proposal is based on the fact that hydrocarbons are eluted in a nonpolar column in the order of their relevant boiling points, and it is therefore possible to convert the retention times into distillation temperatures. In this manner, by using packed columns with nonpolar stationary phases (generally of polydimethylxyloxane type or of the DEXSIL (registered trademark Dexsil Chemical Corporation, Hamden, Conn.) type based on carbonium and silicium), it is possible to obtain a chromatograph representing the sample elution curve wherein each retention time corresponds to a given boiling point. The retention times are converted into boiling points by means of a boiling point-retention time curve plotted by performing a previous calibration with a known standard sample (generally mixtures of normal-alkanes). Once the time axis is calibrated in temperatures, the surface comprised within the elution curve and the base line of the chromatogram is integrated in slices and summed up, thus obtaining the cumulative surfaces corresponding to each boiling temperature. The graphic display of the cumulative surfaces (in percent of the total surface comprised between the elution curve and the base line), as a function of the boiling points, provides a simulated distillation/boiling point distribution curve (similar to the Engler distillation curve).

The technique described above is well known and applied and is already standardized (see ASTM D 2887 "Boiling Range Distribution of Petroleum Fraction by Gas Chromatography"). However, it is also known that this simulated distillation technique, which provides undeniable advantages of time redution (in the order of 1:100) and energy savings in comparison with the conventional distillation, exhibits some limitations when dealing with heavy or high-boiling petroleum samples to be analyzed. In fact, because of the limitations in the highest temperature at which the packed column can be heated and because of the extremely long retention times of high-boiling compounds at the temperatures of the analytical program, it is generally impossible to characterize hydrocarbons having boiling points exceeding approximately 600° C. that correspond to normal alkanes with a number of carbon atoms around 55–60.

OBJECT OF THE INVENTION

The object of this invention is to provide a method and an apparatus for the simulated distillation of petroleum products by gas chromatography wherein such distillation is capable of analyzing heavy petroleum products, such as, for example, residues of distillation under vacuum, containing molecules with a boiling point exceeding of 600° C. and up to 800° C. TPB. Such compounds correspond to normal alkanes containing a number of carbon atoms exceeding 130.

This object is achieved by a simulated distillation method comprising employing gas chromatographic analysis apparatus consisting of a direct nonvaporizing cold on-column injector, a gas chromatographic capillary column with an inner diameter ranging between 0.2 and 0.6 mm and a length between 1 and 10 m, the column having a thin film stationary phase less than or equal to 0.2 $\mu$m, an oven in which the column is housed and which is programmable over 400° C. with a programmation speed equal to at least 5° C./min., and a flame ionization detector; injecting into the direct cold on-column injector an appropriately diluted sample of a petroleum product; performing a gas chromatographic analysis with a temperature program on such sample, possibly ending at temperatures higher than 400° C.; converting the time axis of the obtained chromatogram on such sample boiling point axis by using an adequate calibration mixture that permits the obtaining of a standard curve; and integrating in slices the surface between the sample elution curve and the chromatogram base line to obtain a simulated distillation boiling point distribution curve.

DETAILED DESCRIPTION OF THE INVENTION

Figure 3:
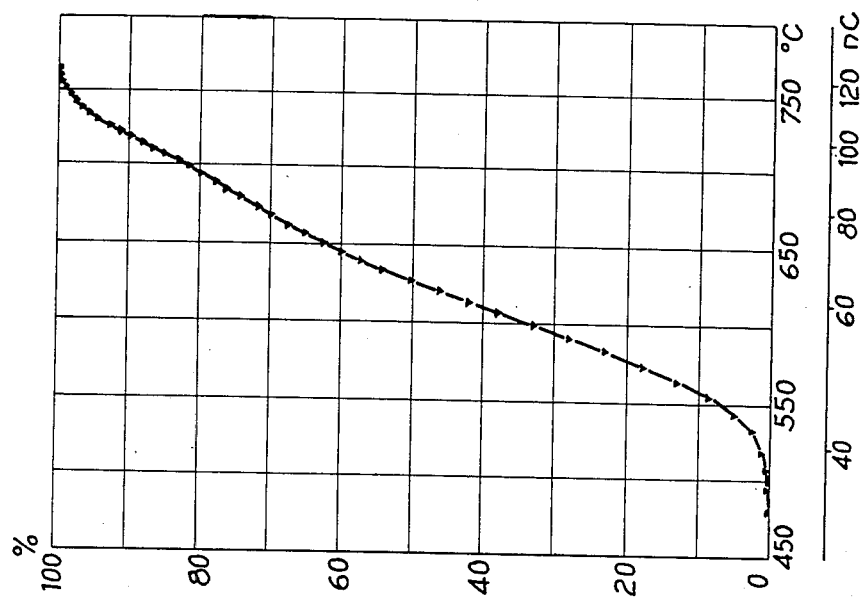
FIG. 3 is a simulated distillation curve generated from the chromatograms illustrated in FIGS. 1 and 2.

The present invention relates not only to a method of developing a simulated distillation curve but also relates to the apparatus utilized in developing such simulated distillation curve using the inventive method. Such apparatus is for gas chromatographic analysis and has a direct nonvaporizing cold on-column injector which is utilized with a gas chromatographic capillary column having an inner diameter dimension ranging between 0.2 and 0.6 mm and a length of 1 to 10 meters. Also contained in the column is a thin film stationary phase that is less than or equal to 0.2 micrometers ($\mu$m). Also used in connection with this gas chromatographic analysis apparatus is an oven that houses the column. The oven is programmable over 400° C. with a programming speed equal to at least 5° C./min. Finally, the gas chromatographic analysis equipment has a flame ionization detector associated therewith. In performing the method appropriately diluted petroleum product sample is injected into the direct cold on-column injector whereby a gas chromatographic analysis is performed on such sample at a temperature programmed in the oven whereby the temperature of the oven will be higher than 400° C. The analysis will yield a chromatogram wherein the time axis of the attained chromatogram is converted into a boiling point axis by using an adequate calibration mixture that allows one to obtain a standard curve. The method is then followed by integrating in slices the surface between the sample elution curve the chromatogram base line to obtain a simulated distillation boiling point distribution curve.

In utilizing the equipment set forth above to perform the method of the present invention, it is advisable that the equipment include a pneumatic system to feed the carrier, which allows said feeding to be performed at a constant pressure during the injection and at a constant flow during the analysis. Moreover, the injected petroleum product sample can be pretreated to remove asphaltenes (if present in the same) and diluted to sample concentrations of approximately 10 grams per liter. Asphaltene removal is carried out by solution in n-heptane followed by filtration of asphaltenes (for example, as described in Standards IP-143/78 or NF-T 60115) and partial evaporation of the solvent, which still remains as sample solvent. It is also possible to operate without deasphaltation, taking into account a presence of dirt in the initial section of the column and using carbon sulfide as solvent.

Finally, the conversion of the chromatogram time into boiling point temperatures is performed by using a standard compound containing heavy alkanes, 80 carbon atoms on the average, or consisting of products such as POLYWAX (registered trademark of BARECO Division of Petrolite Corporation of Tulsa, Okla.) and with extrapolation of the boiling temperature curve in function of retention time in the column.

The method according to the invention, together with the equipment as defined in the aforementioned description, allows one to attain results never achieved up to now in simulated distillation petroleum products with reference to the characterization of high-boiling components, such as compounds with molecules having greater than 55 carbon atoms. These results are obtained based upon the temperature at which the method is performed wherein the temperature is raised above 400° C. and generally up to approximately 430°-450° C. Moreover, the method of the present invention also relies upon the features of the chromatogram column, which is a capillary column and not a packed column. Capillary columns are necessary to achieve the desired results because only by using a capillary column is it possible to obtain a detectable elution of hydrocarbons having over 60 carbon atoms without increasing the oven temperatures above the limits presently imposed by the stationary phase. This is achieved by reducing column retention capacity in two manners. One, the column length and diameter can be altered, and two, the thickness of the stationary phase film can be changed.

The length of the capillary column is kept within the values of 1-10 meters. A column less than 1 meter in length does not provide sufficient power of separation of the compound. A capillary column over 10 meters in length is too long, and therefore, the retention times of the heavy compounds are too high. With respect to the stationary phase present in the gas chromatographic column, such stationary phase can be one of the phases used up to now for simulated distillation (for instance, poly/dimethylsilicones) and forms a thin layer having a thickness less than 0.2 $\mu$m, for example, 0.1 $\mu$m. By having such a stationary phase, it is possible to reduce the elution time of the high boiling compounds with respect to known simulated distillations providing the possibility to analyze hydrocarbons having over 100 carbon atoms using the present invention.

In choosing a standard petroleum compound to convert the retention times to boiling points, one must use a standard to cover the range of compounds of greater than 55 carbon atoms. Suggested standards for this purpose are polyethylenes having average molecular weight from 500-1500. An example of such a compound is sold under the registered trademark POLYWAX. It must be realized that the boiling points of polyethylenes containing more than 60 carbon atoms are calculated by extrapolation of the curves obtained by plotting the boiling points of n-alkanes as a function of the number of carbon atoms of such polyethylenes.

When performing the present invention, it is necessary when injecting the sample into the column that such injection take place without discrimination and in such a manner that polluting components are not introduced. The use of vaporizing conventional injectors having septums are therefore excluded, since the chromatogram that would result from such an analysis concerning the decomposition products would include septum fractions that would enter the vaporizer. Furthermore, the injection of the sample into a heated environment to produce vaporization causes the discrimination of high-boiling-point compounds, which vapors remain partly in the syringe needle or in the heated sampling system.

By utilizing a nonvaporizing direct cold on-column injector, it has been shown that such injector is appropriate, since this injector ensures that the whole liquid sample enters the column. The only problem that might be experienced with such an injector is the possibility that very heavy compounds remain in the starting point of the column, which compounds are not eluted and can therefore damage the column. This problem is solved by periodically physically eliminating the column section involved or by submitting the column to a deasphaltation treatment. In such cases it is advisable that a starting part of the capillary column—for example, approximately 1 m long—be empty and deactivated.

The capillary column can be made of glass, metal (for example, nickel), or fused silica. In terms of the dimensions of the column, the column should have an inner diameter exceeding 0.2 mm to allow the introduction of the needle but less than 0.6 mm to avoid problems of pressure fall in the column itself and to maintain a certain separatory power of the same. In the case of fused silica columns, which have an external polyimide coating, it must be remembered that the coating oxidizes at temperatures exceeding 380°–400° C. Therefore, there must be an atmosphere of inert gas in the oven to prevent this, or else the fused silica columns should be coated with metal instead of with polyimide.

Because of the use of short columns, it is difficult to control the pressure fall along the column. However, in any case, such pressure fall remains low. To overcome this problem, a nonvaporizing direct on-column injector is used with a carrier gas fed at a constant pressure during the sample injection state and at a constant flow in the subsequent state of chromatographic analysis. The preferred carrier gas is hydrogen, whose optimal flow is at least double that of all other gases, which allows reduction in the elution times. However, it also should be realized that inert gases such as helium can be used.

The detector utilized with the present invention is of the flame ionization type (FID-Flame Ionization Detector). As it is known, the response of this type of detector strongly varies with the hydrogen flow, which is the preferred carrier gas. The use of hydrogen and of oven temperatures programmed up to temperatures exceeding 400° C. result in a decrease of hydrogen flow through the column if the carrier gas is fed at a constant pressure. This variation produces a change in the detector response with the oven temperature and therefore introduces an error factor in the results. Therefore, in order to eliminate this drawback, it is necessary to use a pneumatic system allowing a carrier gas to be fed at a constant flow during the analysis. Finally, the flame ionization detector body between the outlet port of the gas chromatographic column from the oven and the detector flame is heated by suitable means in order to avoid colder points with respect to the temperature set for the detector and the maximum programmed temperature for the oven.

In order to show the advantageous features of the present invention, the result of an analysis as performed on a sample consisting of a deasphalted residue under vacuum with an initial boiling point at approximately 550° C. is hereinafter reported.

Figure 1:
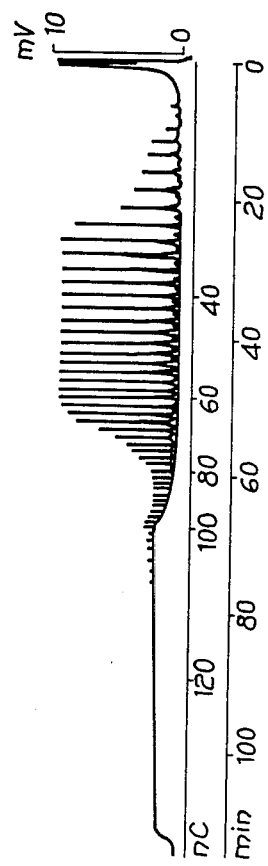
FIG. 1 is a chromatogram of a petroleum residue sample generated by utilizing the method of the present invention.
Figure 2:
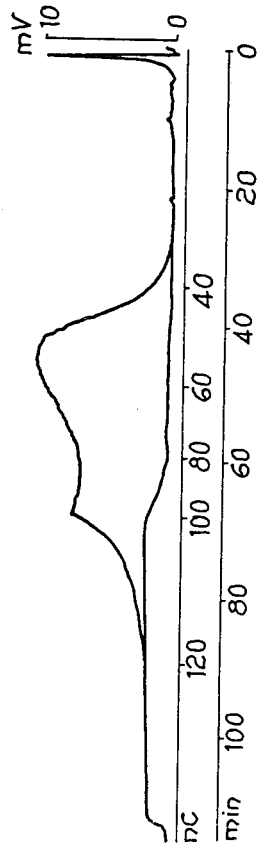
FIG. 2 is a chromatograph of a known standard sample generated by using the method of the present invention.

The analytical equipment used in this procedure was the following: A gas chromatographic apparatus type Mega HT of Carlo Erba Strumentazione S.p.A. with a nonvaporizing direct on-column injector, of the type shown in U.S. Pat. No. 4,269,608, the description of which is incorporated herein by reference thereto, and in this case of type OC 50; a column with inner diameter of 0.32 mm having an empty and deactivated initial section of 1.00 m and a length of the following part, bearing the stationary phase of 9.00 m. The stationary phase consisted of polydimethylsilicones in a layer of about 0.08 $\mu$m thickness. The temperature program of the oven was performed starting from 60° C. up to 430° C. at a rate of 5° C. per minute. The chromatogram of the deasphalted residue having an initial boiling point at approximately 550° C. is shown in FIG. 1 and was obtained using the above apparatus. The curve reported in FIG. 2 was obtained by using a standard consisting of POLYWAX 655 using the above apparatus. The chromatogram of FIG. 1 was then conventionally processed on the basis of the curve of FIG. 2 to obtain the simulated distillation curve as reported in FIG. 3.

Although particular embodiments of the invention have been shown and described, it is to be understood that the scope of the invention is not limited to these embodiments, since modifications can be made by one skilled in the art.

We claim:

1. A method of the simulated distillation of petroleum products utilizing apparatus adapted for chromatographic analysis including a capillary column wherein said capillary column has an inner diameter ranging between 0.2 and 0.6 mm and a length between 1 and 10 m, said capillary column having therein a thin film stationary phase less than or equal to 0.2 $\mu$m, said capillary column having a first end and a second end and having associated with said first end of said capillary column a direct nonvaporizing cold on-column injector and an oven in which said capillary column is housed, said oven being programmable to reach temperatures over 400° C. at a speed equal to at least 5° C. per minute and wherein said apparatus has a flame ionization detector connected to said second end of said column, said method comprising the steps of:
  (a) injecting into said column utilizing said direct cold on-column injector an appropriately diluted sample of a sample petroleum product;
  (b) performing a gas chromatographic analysis on said sample petroleum product using said apparatus at a preprogrammed temperature having a temperature end point greater than 400° C.;
  (c) converting said time axis of said chromatogram obtained from said gas chromatographic analysis of said sample petroleum product into a boiling point axis by using a standard calibration mixture which generates a standard curve; and
  (d) integrating in slices the surface between the sample elution curve and the chromatogram base line to obtain a simulated distillation boiling point distribution curve.

2. The method according to claim 1 including feeding a carrier gas into said column.

3. The method according to claim 1 wherein said carrier gas is hydrogen or helium.

4. The method according to claim 2 wherein said feeding of said carrier gas into said column is carried out by feeding said carrier gas at a constant pressure during said injecting and at a constant flow during said gas chromatographic analysis.

5. The method according to claim 1 wherein the step of obtaining a standard curve comprises extrapolating a curve of boiling points of n-alkanes with respect to the number of carbon atoms of said n-alkanes.

6. The method according to claim 1 wherein said capillary column is formed of fused silica with a polyimide coating.

7. The method according to claim 6 comprising the step of feeding an inert gas into said oven prior to said chromatographic analysis.

8. The method according to claim 1 wherein said standard calibration mixture has a molecular weight from about 500 to 150.

9. The method according to claim 1 comprising the further step of performing a deasphaltation step on said sample petroleum product prior to injecting said petroleum product sample into said column for chromatographic analysis.

* * * * *

UNITED STATES PATENT AND TRADEMARK OFFICE
CERTIFICATE OF CORRECTION

PATENT NO. : 4,757,023
DATED : July 12, 1988
INVENTOR(S) : Sorin Trestianu et al It is certified that error appears in the above-identified patent and that said Letters Patent is hereby corrected as shown below:

Column 2, line 24, "redution" should read --reduction--.
Column 6, line 57, "claim 1" should read --claim 2--.
Column 8, line 2, "150" should read --1500--.

Signed and Sealed this

Twenty-ninth Day of November, 1988

Attest:

DONALD J. QUIGG

*Attesting Officer*  *Commissioner of Patents and Trademarks*